(12) United States Patent
Cremer et al.

(10) Patent No.: US 8,337,569 B2
(45) Date of Patent: Dec. 25, 2012

(54) POLYMERIC HAIR DYES

(75) Inventors: Christian Cremer, Lörrach (DE);
Oliver Becherer, Schwörstadt (DE);
Beate Fröhling, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/381,967

(22) PCT Filed: Jul. 15, 2010

(86) PCT No.: PCT/EP2010/060175
§ 371 (c)(1),
(2), (4) Date: Jan. 23, 2012

(87) PCT Pub. No.: WO2011/006946
PCT Pub. Date: Jan. 20, 2011

(65) Prior Publication Data
US 2012/0110750 A1    May 10, 2012

(30) Foreign Application Priority Data

Jul. 15, 2009   (EP) ..................... 09165528

(51) Int. Cl.
*A61Q 5/10*    (2006.01)
*C07D 213/00*  (2006.01)

(52) U.S. Cl. ............. 8/405; 8/406; 8/552; 8/554; 8/647; 546/264

(58) Field of Classification Search .............. 8/405, 406, 8/552, 554, 647; 546/264
See application file for complete search history.

(56) References Cited

U.S. PATENT DOCUMENTS

| | | | |
|---|---|---|---|
| 4,182,612 A | 1/1980 | Sokol et al. | |
| 4,228,259 A | 10/1980 | Kalopissis et al. | |
| 4,763,371 A | 8/1988 | Parton | |
| 5,125,930 A * | 6/1992 | Taniguchi ........................ | 8/655 |
| 5,547,790 A | 8/1996 | Umeda et al. | |
| 2009/0255063 A1 | 10/2009 | Marquais-Bienewald et al. | |
| 2010/0192312 A1 | 8/2010 | Cremer et al. | |
| 2011/0061179 A1 | 3/2011 | Cremer | |
| 2011/0061180 A1 | 3/2011 | Cremer | |
| 2011/0088173 A1 | 4/2011 | Marquais-Bienewald | |
| 2011/0296631 A1 | 12/2011 | Marquais-Bienewald | |

FOREIGN PATENT DOCUMENTS

| | | | |
|---|---|---|---|
| EP | 0205291 A2 | 12/1986 | |
| FR | 2456764 | 5/1979 | |
| GB | 2440219 A | 1/2008 | |
| JP | 58 011516 A | 1/1983 | |
| WO | 2008/009579 A1 | 1/2008 | |
| WO | 2008/138726 A2 | 11/2008 | |

OTHER PUBLICATIONS

STIC Search Report dated Aug. 22, 2012.*
Patent Abstracts of Japan 58011516, (1983).
English Language Abst. of FR 2456764,(1979).

* cited by examiner

*Primary Examiner* — Eisa Elhilo
(74) *Attorney, Agent, or Firm* — Shiela A. Loggins

(57) ABSTRACT

Disclosed are polymeric dyes of formula (1a), (1b), or (1c); wherein the substituents and variables are defined in the claims and specification. The dyes are distinguished by their depth of shade and their good fastness properties to washing, such as, for example, fastness to light, shampooing and rubbing.

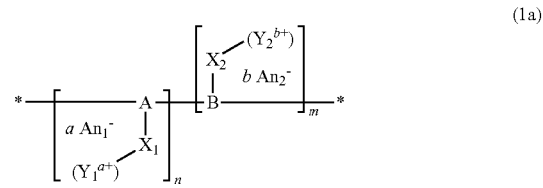

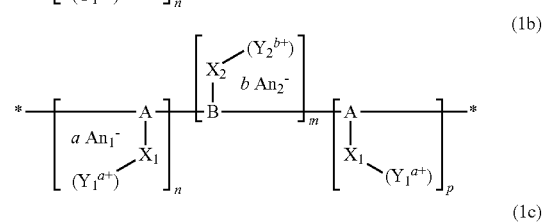

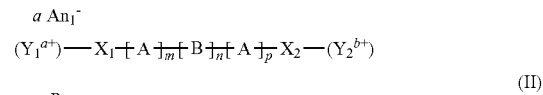

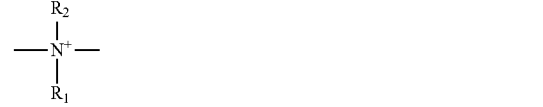

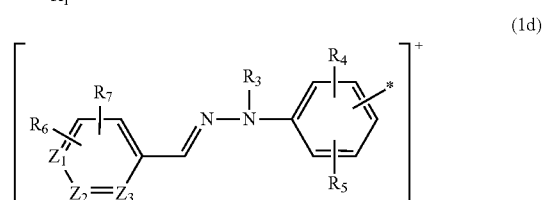

17 Claims, No Drawings

POLYMERIC HAIR DYES

The present invention relates to novel polymeric dyes and compositions comprising these compounds, to a process for their preparation and to their use for dyeing of organic materials, such as keratin-containing fibers, leather, silk, cellulose or polyamides, natural and synthetic fibers like wool or polyacrylnitril, paper or wood.

They also can be used in the form of printing inks, printing dyes or coating compositions.

It is well known that cationic compounds have a good affinity to negative charged hair. These characteristics have been used to contact the hair with small molecules, but also with polymers.

Numerous cationic polymeric dyes have been disclosed for use as a colorant for human hair, for example in U.S. Pat. No. 4,228,259, U.S. Pat. No. 4,182,612 or FR 2 456 764. These references teach that the polymer moiety has the cationic charge.

Surprisingly it was found that very good dyeing results are obtained with polymeric hair dyes wherein the cationic charge is located in dye moiety.

Therefore the present invention relates to polymeric dyes of formula (1a)

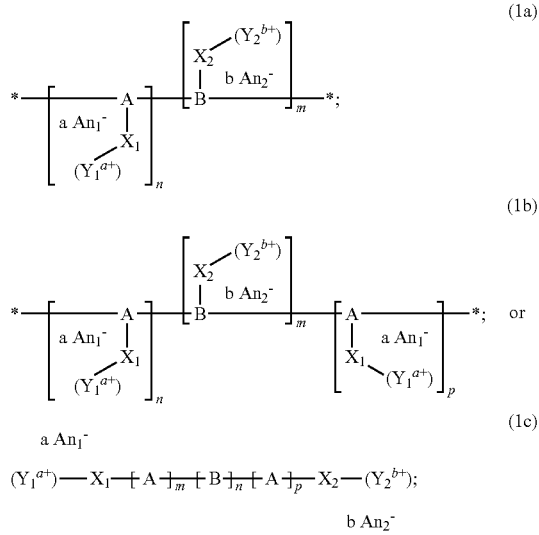

wherein

A and B, independently from each other represent a polymer backbone;

$X_1$ and $X_2$ independently from each other are a linkage group selected from —S—, —S—S—, —N—, —N═, —N($R_5$)—, —S(O)—, —SO$_2$—, —(CH$_2$CH$_2$—O)$_{1-5}$—, —(CH$_2$CH$_2$CH$_2$—O)$_{1-5}$—, —C(O)—, —C(O)O—, —OCO—,

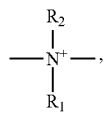

—CON($R_1$)—, —C(NR$_1$R$_2$)$_2$—, —(R$_1$)NC(O)—, —C(S)R$_1$—; which may be interrupted and/or terminated at one or both ends by one or more than one —C$_1$-C$_{30}$alkylene- or —C$_2$-C$_{12}$alkenylene-; or an optionally substituted, saturated or unsaturated, fused or non-fused aromatic or nonaromatic (heterocyclic) bivalent radical optionally comprising at least one heteroatom; a saturated or unsaturated, fused or non-fused aromatic or nonaromatic bivalent radical comprising at least one heteroatom, which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), hydroxy or halogen;

$R_1$ and $R_2$ independently from each other are hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);

$Y_1$ and $Y_2$ independently from each other are a residue of an organic dye selected from hydrazone dyes of formula

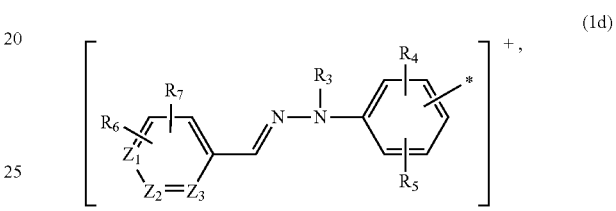

wherein $Z_1$, $Z_2$ and $Z_3$, independently from each other are —CR$_8$— or —NR$_9^+$—; and at least one of $Z_1$, $Z_2$ or $Z_3$ is —NR$_9^+$—, wherein at least one of $Y_1$ and $Y_2$ is a residue of an organic dye;

R, $R_3$, $R_4$, $R_5$, $R_6$, $R_7$, $R_8$ and $R_9$ independently from each other are hydrogen; hydroxy; $C_1$-$C_5$alkyl; hydroxy-$C_1$-$C_5$alkyl; $C_1$-$C_5$alkoxy; —NO$_2$; —Cl; —Br; —COOH; —SO$_3$H; —CN; NH$_2$; or CH$_3$—CO—NH—;

An$_1$, An$_2$ and An$_3$, independently from each other are an anion;

a and b independently from each other are a number from 1 to 3;

m is a number from 0 to 5000;

n is a number from 0 to 5000; and p is a number from 1 to 5000;

wherein the sum of m+n+p≧3.

$C_1$-$C_{14}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecy, dodecyl, tredecyl or tetradecyl.

$C_2$-$C_{14}$alkenyl is for example allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

$C_6$-$C_{10}$aryl is for example phenyl or naphthyl.

$C_1$-$C_{30}$alkylene is for example methylene, ethylene, propylene, isopropylene, n-tetramethylene, sec-tetramethylene, tert-tetramethylene, n-pentamethylene, 2-pentamethylene 3-pentamethylene, 2,2'-dimethylpropylene, cyclopentamethylene, cyclohexamethylene, n-hexamethylene, n-octamethylene, 1,1',3,3'-tetramethyltetramethylene, 2-ethylhexamethylene, nonamethylene, decamethylene, tridecamethylene, tetradecamethylene, pentadecamethylene, hexadecamethylene, heptadecamethylene, octadecamethylene, nonadecamethylene or eicosamethylene.

Preferred are dyes of formal (1a), (1b) or (1c), wherein $Y_1$ and $Y_2$ correspond to the formula

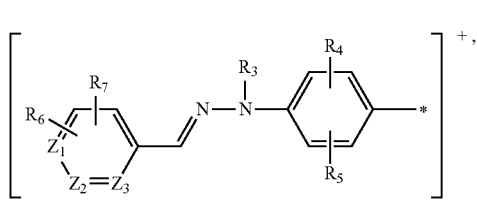

(1e)

wherein
$Z_1$, $Z_2$ and $Z_3$, R, $R_3$, $R_4$, $R_5$, $R_6$, $R_7$, and $R_8$ are defined as in (1a), (1b) or (1c).

More preferred are dyes of formulae (1a), (1b) and (1c), wherein
$Y_1$ and $Y_2$ correspond to the formula

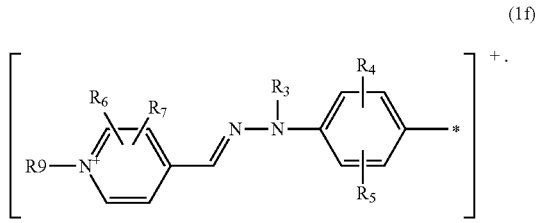

(1f)

Most preferably $Y_1$ and $Y_2$ have the same meaning.
Preferably $X_1$ and $X_2$ independently from each other are a linkage group selected from —$SO_2$— and —C(O)—.
Preferably in formulae (1a), (1b) and (1c)
A and B, independently from each other are selected from polyethyleneimine, polypropyleneimine, polyvinylamine; polyvinylimine; polysiloxane; polystyrene, polyvinylimidazol, polyvinylpyridine, copolymers of vinylimidazole or vinylpyridin and vinylpyrrolidone, DADMAC/DAA copolymers, polyetheramines, polyvinylalcohol, polyacrylate, polymethacrylate; polyguanidines, polyurethanes derived from hydroxyl-terminated polyethers, polyesters or polybutadienes on the one hand and aliphatic or aromatic polyisocyanates on the other, as well as precursors thereof; polyamides and copolyamides derived from diamines and dicarboxylic acids and/or from aminocarboxylic acids or the corresponding lactams; polysaccharide, starch, cellulose, lignin; and copolymers and blends of the mentioned polymers.

Especially preferred are polyethyleneimine, polyvinylamine, polyetheramines, Polyethyleneimines can be prepared by known procedures as describes in Römpps Chemie Lexikon, 8. Aufl. 1992, S. 3532-3533 or in Ullmanns Enzyklopädie der Technischen Chemie, 4. Aufl. 1974, Bd. 8, S. 212-213. They have a molecular weight in the range of 200 bis 1 000 000 g/mol. Trade names are for example Lupasol® from BASF SE or Epomin from Nippon Shokubai.

Also preferred are polyamidoamines or polyvinylamines grafted with ethylenimine Homopolymers and copolymers mentioned above may have any stereostructure including syndiotactic, isotactic, hemi-isotactic or atactic; where atactic polymers are preferred. Stereoblock polymers are also included.

Examples for halogen-containing polymers are polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

Examples for polymers derived from α,β-unsaturated acids and derivatives thereof are polyacrylates and polymethacrylates; polymethyl methacrylates, polyacrylamides and polyacrylonitriles, impact-modified with butyl acrylate.

Examples for copolymers of the monomers mentioned above with each other or with other unsaturated monomers are acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

Examples for polymers derived from unsaturated alcohols and amines or the acyl derivatives or acetals thereof are for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in above.

Examples for homopolymers and copolymers of cyclic ethers are polyalkylene glycols, polyethylene oxide, polypropylene oxide or copolymers thereof with bisglycidyl ethers.

Examples for polyacetals are polyoxymethylene and those polyoxymethylenes which contain ethylene oxide as a comonomer; polyacetals modified with thermoplastic polyurethanes, acrylates or MBS.

Examples for polyamides and copolyamides derived from diamines and dicarboxylic acids and/or from aminocarboxylic acids or the corresponding lactams are polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

Examples for natural polymers are cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

Preferably both the polymer backbone (A and B) and residue of an organic dye ($Y_1$ and $Y_2$) have a functional group selected from the electophilic group selected from halide, tosylate, mesylate, methoxy, acid chloride, sulfonyl chloride, epoxides, anhydride; or a nucleophilic group selected from amine, hydroxyl and thiol.

Preferably the molecular weight of the polymeric dye is from 400 to 50000.

"Anion" denotes, for example, an organic or inorganic anion, such as halide, preferably chloride and fluoride, sulfate, hydrogen sulfate, phosphate, boron tetrafluoride, carbonate, bicarbonate, oxalate or $C_1$-$C_8$alkyl sulfate, especially methyl sulfate or ethyl sulfate; anion also denotes lactate, formate, acetate, propionate or a complex anion, such as the zinc chloride double salt.

Most preferred are dyes of formula

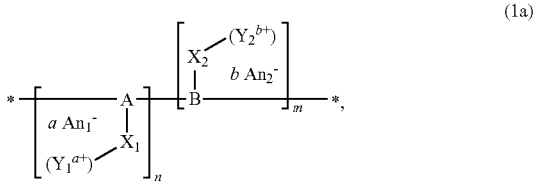

wherein

A and B, independently from each other represent a polymer backbone;

$X_1$ and $X_2$ independently from each other are a linkage group selected from —$SO_2$— and —C(O)—;

$Y_1$ and $Y_2$ independently from each other are a radical of formula (1f);

a and b independently from each other are a number from 1 to 3;

m is a number from 0 to 5000;

n is a number from 0 to 5000; and wherein the sum of m+n≧2.

A further embodiment of the present invention relates to processes for the preparation of the dyes of formula (1a), (1b) and (1c).

Generally, the process comprises a) first the synthesis of a hydrazone dye of formula (1d) and then the reaction with a polymer comprising at least one nucleophilic functionality or b) first reaction of the phenyl building block of the hydrazone dye with a polymer comprising at least one nucleophilic functionality and then the preparation of the hydrazone dye on the polymer bound phenyl moiety.

For both routes a) or b) the phenyl moiety of the hydrazone chromophores contains at least one electrophilic functionality, to react with a polymer comprising at least one nucleophilic functionality, which can be selected from acetate, brosylat, mesylat, nosylat, tosylat, trifluoracetat, trifluorsulfonat, chlor, brom or iod, sulfate esters, vinylsulfones, carboxylic acids, their esters or acid chlorides, epoxides or halohydrineethers.

The synthetic procedures for the preparation of the hydrazone chromophore are described for example in Ullmann's Encyclopedia of Industrial Chemistry, chapter on Methine Dyes and Pigments, 6.2.2.

The reactions are generally initiated by contacting; for example by mixing together the starting compounds or by dropwise addition of one starting compound to the other.

Customary, the temperature is in the range of 273 to 423 K, preferably is in the range of 290 to 300 K during the mixing of the starting compounds.

The reaction time is generally dependent on the reactivity of the starting compounds, on the reaction temperature chosen and on the desired conversion. The chosen duration of reaction is usually in the range from one hour to three days.

The reaction temperature for the reaction of the compounds is advisable to select in the range from 273 to 423K, especially in the range from 273 to 335K.

The reaction pressure chosen is generally in the range from 70 kPa to 10 MPa, especially from 90 kPa to 5 MPa, and is more especially atmospheric pressure.

It may by desirable to conduct the reaction of compounds in the presence of a catalyst.

The molar ratio of compound of formula (1a) to the catalyst is generally selected in the range from 10:1 to 1:5, especially in the range from 10:1 to 1:1.

Suitable catalysts are for example an alkali metal $C_1$-$C_6$alkyloxide, such as sodium-, potassium or lithium $C_1$-$C_6$alkyloxide, preferably sodium methoxide, potassium methoxide or lithium methoxide, or sodium ethoxide, potassium ethoxide or lithium ethoxide; or tertiary amines, for example, such as chinuclidine, N-methylpiperidine, pyridine, trimethylamine, triethylamine, trioctylamine, 1,4-diazabicyclo[2.2.2]octan, chinuclidine, N-methylpiperidine; or alkali-metal acetate, for example such as sodium acetate, potassium acetate, or lithium acetate.

Preferred are potassium acetate, sodium methoxide, pyridine and 1,4-diazabicyclo[2.2.2]octan.

In addition, the reactions may be carried out with or without a solvent, but are preferably carried out in the presence of a solvent.

Solvents are organic solvents and water, or a mixture of organic solvents or a mixture of organic solvents and water.

Organic solvents are for example, protic or aprotic polar organic solvents, such as alcohols, for example methanol, ethanol, n-propanol, isopropanol, butanol or glycols, especially isopropanol, or nitrile, such as acetonitrile or propionitrile, or amide, such as dimethyl-formamide, dimethylacetamide or N-methylpyridine, N-methylpyrolidon, or sulfoxide, such as dimethylsulfoxide, or mixtures thereof.

The product prepared according to the process of the present invention may be advantageously worked up and isolated, and if desired be purified.

Customary, the work up starts by decreasing the temperature of the reaction mixture in the range from 280 to 300 K, especially in the range from 290 to 300 K.

It may be of advantageous to decrease the temperature slowly, over a period of several hours.

For the isolation it may also be advantageous to add organic or inorganic acids, like hydrochloric acid, methanesulfonic acid, acetic acid or formic acid to the reaction mixture.

In general, the reaction product is usually filtered and then washed with water or a salt solution and subsequently dried.

Filtration is normally carried out in standard filtering equipment, for example Büchner funnels, filter presses, pressurised suction filters, preferably in vacuo.

The temperature for the drying is dependent on the pressure applied. Drying is usually carried out in vacuo at 50-200 mbar.

The drying is usually carried out at a temperature in the range from 313 to 363 K, especially from 323 to 353 K, and more especially in the range from 328 to 348 K.

Advantageously the product is purified by recrystallisation after isolation.

Organic solvents and solvent mixtures are suitable for the recrystallisation, preferably alcohols, for example methanol, ethanol, 2-propanol or butanol, especially 2-propanol.

The hydrazone compounds of the formula (1a), (1b), (1c) are used, in particular, as dyes for dyeing and printing textile materials, paper and leather and for the preparation of inks.

Suitable textile materials are natural and synthetic materials which can be dyed by cationic processes. The novel hydrazone compounds are preferably employed for dyeing and printing paper, thin cardboard and cardboard in the pulp and on the surface, and also textile materials which, for example, advantageously consist of homopolymers or copolymers of acrylonitrile or of synthetic polyamides or polyesters modified with acid groups. These textile materials are preferably dyed in an aqueous, neutral or acid medium by the exhaust method, if appropriate under pressure, or by the continuous method. In this regard, the textile material can be in a very wide variety of different forms, for example as fibres, filaments, woven fabrics, knitted fabrics, piece goods and made-up articles, such as shirts or pullovers.

The dyes according to the invention make it possible to produce level dyeings or prints which are distinguished by very good overall fastness properties, in particular a very high degree of exhaustion and good fastness properties to water.

Furthermore, the novel hydrazone compounds of the formula (1a), (1b), (1c) can also be used for dyeing and printing natural and regenerated cellulose materials, in particular cotton and viscose, deeply coloured dyeings also being obtained.

On these textile materials, the novel hydrazone compounds of the formula (1a), (1b), (1c) have a good substantially a good degree of exhaustion, and the dyeings obtained exhibit very good fastness properties, in particular fastness to wet processing.

A preferred use of the novel hydrazone compounds of the formula (1a), (1b), (1c) is their use for dyeing paper of all kinds, in particular bleached, unsized and sized, lignin-free paper, it being possible to use bleached or unbleached pulp as the starting material and to use hardwood pulp or softwood pulp, such as birch and/or pine sulfite and/or sulfate pulp. These compounds are very particularly suitable for dyeing unsized paper (for example table napkins, table cloths and hygiene papers) as a result of their very high affinity for this substrate.

The novel hydrazone compounds of the formula (1a), (1b), (1c) are very strongly absorbed onto these substrates, the effluents remaining virtually colourless. Dyeings in yellow, green-yellow or orange shades are obtained.

The dyeings obtained are distinguished by good overall fastness properties, such as good fastness to light, and at the same time have a high clarity and depth of colour and fastness to wet processing, i.e. they exhibit no tendency to bleeding when dyed paper is brought into contact under wet conditions with moist white paper. In addition they exhibit good fastness to alum, acids and alkalis. The fastness to wet processing relates not only to water, but also to milk, fruit juices and sweetened mineral water; owing to their good fastness to alcohol, the dyes are also fast to alcoholic beverages. This property is particularly desirable, for example, for table napkins and table cloths in the case of which it can be expected that the dyed paper will come into contact in a wet state (for example impregnated with water, alcohol, surfactant solution etc.) with outer surfaces, such as textiles, paper and the like, which must be protected against soiling.

The high affinity for paper and the high exhaustion rate of the novel dyestuffs is of great advantage for the continuous dyeing of paper.

The dyeings obtained on hair are distinguished by their depth of shade and their good fastness properties to washing, such as, for example, fastness to light, shampooing and rubbing.

Generally, hair dyeing agents on a synthetic base may be classified into three groups:
  temporary dyeing agents
  semipermanent dyeing agents, and
  permanent dyeing agents.

The multiplicity of shades of the dyes can be increased by combination with other dyes.

Therefore the dyes of formula (1a), (1b) and (1c) of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Especially preferred is the combination of the dyes of formula (1a), (1b) and (1c) with other polymeric dyes as described in GB 2440219, WO 09/090,121, WO 09/090,122, WO 09/090,124 or WO 09/090,125.

Direct dyes are of natural origin or may be prepared synthetically. They are uncharged, cationic or anionic, such as acid dyes.

The dyes of formula (1a), (1b) and (1c) may be used in combination with at least one single direct dye different from the dyes of formula (1a), (1b) and (1c).

The inventive polymeric hair dyes do not require any addition of an oxidizing agent to develop their dyeing effect. This fact could possibly reduce the damage of the hair. In addition many of the perceived or documented disadvantages of current oxidative hair dyes like their skin irritation, skin sensibilization and allergenic properties can be prevented by the use of the inventive hair dyes. Also, the inventive hair dyes are easier to apply and to use in formulations than oxidative hair dyes since no chemical reaction occurs upon application on the head. Especially advantageous is the fact, that the dyeing time is significantly shorter (ca. 5-10 min) than dyeing using oxidative dyes.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europaisches Inventar der Kosmetikrohstoffe", 1996, published by The European Commission, obtainable in diskette form from the Bundesverband der deutschen Industrie-und Handelsunternehmen für Arzneimittel, Reformwaren und Körperpflegemittel e.V., Mannheim.

More preferred direct dyes which are useful for the combination with at least one single dye of formula (1a), (1b) and (1c), especially for semi permanent dyeing, are: 2-amino-3-nitrophenol, 2-amino-4-hydroxyethylamino-anisole sulfate, 2-amino-6-chloro-4-nitrophenol, 2-chloro-5-nitro-N-hydroxyethylene-p-phenylendiamine, 2-hydroxyethyl-picramic acid, 2,6-diamino-3-((pyridine-3yl)-azo)pyridine, 2-nitro-5-glyceryl-methylanil, 3-methylamino-4-nitro-phenoxyethanol, 4-amino-2-nitrodiphenyleneamine-2'-carboxilic acid, 6-nitro-1,2,3,4,-tetrahydroquinoxal, 4-N-ethyl-1,4-bis(2'-hydroxyethylamino-2-nitrobenzene hydrochloride, 1-methyl-3-nitro-4-(2'-hydroxyethyl)-aminobenzene, 3-nitro-p-hydroxyethylaminophenol, 4-amino-3-nitrophenol, 4-hydroxypropylamine-3-nitrophenol, hydroxyanthrylaminopropylmethyl morphlino methosulfate, 4-nitrophenyl-aminoethylurea, 6-nitro-p-toluidine, Acid Blue 62, Acid Blue 9, Acid Red 35, Acid Red 87 (Eosin), Acid Violet 43, Acid Yellow 1, Basic Blue 3, Basic Blue 6, Basic Blue 7, Basic Blue 9, Basic Blue 12, Basic Blue 26, Basic Blue 99, Basic Brown 16, Basic Brown 17, Basic Red 2, Basic Red 22, Basic Red 76, Basic Violet 14, Basic Yellow 57, Basic Yellow 9, Disperse Blue 3, Disperse Orange 3, Disperse Red 17, Disperse Violet 1, Disperse Violet 4, Disperse Black 9, Fast Green FCF, HC Blue 2, HC Blue 7, HC Blue 8, HC Blue 12, HC Orange 1, HC Orange 2, HC Red 1, HC Red 10-11, HC Red 13, HC Red 16, HC Red 3, HC Red BN, HC Red 7, HC Violet 1, HC Violet 2, HC Yellow 2, HC Yellow 5, HC Yellow 5, HC Yellow 6, HC Yellow 7, HC Yellow 9, HC Yellow 12, HC Red 8, hydroxyethyl-2-nitro-p-toluidine, N,N-Bis-(2-Hydroxyethyl)-2-nitro-p-phenylendiamine, HC Violet BS, Picramic Acid, Solvent Green 7.

Furthermore, the dyes of formula (1a), (1b) and (1c) may be combined with at least one cationic azo dye, for example the compounds disclosed in GB-A-2 319 776 as well as the oxazine dyes described in DE-A-299 12 327 and mixtures thereof with the other direct dyes mentioned therein, and even more preferred with cationic dyes such as Basic Yellow 87, Basic Orange 31 or Basic Red 51, or with cationic dyes as described in WO 01/66646, especially example 4, or with cationic dyes as described in WO 02/31056, especially example 6, the compound of formula 106; or the cationic dye of formula (3) as described in EP-A-714,954, or with a yellow cationic dye of formula The dyes of formula (1a), (1b) and (1c) may also be combined with acid dyes, for example the dyes which are known from the international names (Color index), or trade names. Preferred acid dyes which are useful for the combination with a dye of formula (1a), (1b) and (1c) are described in U.S. Pat. No. 6,248,314. They include Red Color No. 120, Yellow Color No. 4, Yellow Color No. 5, Red Color No. 201, Red Color No. 227, Orange Color No. 205, Brown Color No. 201, Red Color No. 502, Red Color No. 503, Red Color No. 504, Red Color No. 506, Orange Color No. 402, Yellow Color No. 402, Yellow Color No. 406, Yellow Color No. 407, Red Color No. 213, Red Color No. 214, Red Color No. 3, Red Color No. 104, Red Color No. 105(1), Red Color No. 106, Green Color No. 2, Green Color No. 3, Orange Color No. 207, Yellow Color No. 202(1), Yellow Color No. 202(2), Blue Color No. 202, Blue Color No. 203, Blue Color No. 205, Blue Color No. 2, Yellow Color No. 203, Blue Color No. 201, Green Color No. 201, Blue Color NO. 1, Red Color No. 230(1), Red Color No. 231, Red Color No. 232, Green Color No. 204, Green Color No. 205, Red Color No. 401, Yellow Color No. 403(1), Green Color No. 401, Green Color No. 402, Black Color No. 401 and Purple Color No. 401, especially Black Color No. 401, Purple Color 401, Orange Color No. 205.

These acid dyes may be used either as single component or in any combination thereof.

The dyes of formula (1a), (1b) and (1c) may also be combined with uncharged dyes.

Furthermore, the dyes of formula (1a), (1b) and (1c) may also be used in combination with oxidation dye systems.

Oxidation dyes, which, in the initial state, are not dyes but dye precursors are classified according to their chemical properties into developer and coupler compounds.

Suitable oxidation dyes are described for example in
DE 19 959 479, especially in col 2, l. 6 to col 3, l. 11;
"Dermatology", edited by Ch. Culnan, H. Maibach, Verlag Marcel Dekker Inc., New York, Basle, 1986, Vol. 7, Ch. Zviak, The Science of Hair Care, chapter 8, on p. 264-267 (oxidation dyes);

Preferred developer compounds are for example primary aromatic amines, which are substituted in the para- or ortho-position with a substituted or unsubstituted hydroxy- or amino residue, or diaminopyridine derivatives, heterocyclic hydrazones, 4-aminopyrazol derivatives, 2,4,5,6-tetraminopyrimidine derivatives, or unsaturated aldehydes as described in DE 19 717 224, especially on p. 2, l. 50 to l. 66 and on p. 3 l. 8 to l. 12, or cationic developer compounds as described in WO 00/43367, especially on p., 2 l. 27 to p. 8, l. 24, in particular on p. 9, l. 22 to p. 11, l. 6.

Furthermore, developer compounds in their physiological compatible acid addition salt form, such as hydrochloride or sulfate can be used. Developer compounds, which have aromatic OH radicals are also suitable in their salt form together with a base, such as alkali metal-phenolates.

Preferred developer compounds are disclosed in DE 19959479, p. 2, l. 8-29.

More preferred developer compounds are p-phenylendiamine, p-toluoylendiamine, p-, m- o-aminophenol, N,N-bis-(2-hydroxyethyl)-p-phenylenediamine sulfate, 2-amino-4-hydroxyethylamino-anisole sulfate, hydroxyethyl-3,4-methylendioxyanil, 1-(2'-hydroxyethyl)-2,5-diaminobenzene, 2,6-dimethoxy-3,5-diamino-pyridine, hydroxypropyl-bis-(N-hydroxyethyl-p-phenylenediamine) hydrochloride, hydroxyethyl-p-phenylenediamine sulfate, 4-amino-3-methylphenol, 4-methylaminophenol sulfate, 2-aminomethyl-4-aminophenol, 4,5-diamino-1-(2-hydroxyethyl)-1H— pyrazol, 4-amino-m-cresol, 6-amino-m-cresol, 5-amino-6-chloro-cresol, 2,4,5,6-tetraminopyrimidine, 2-hydroxy-4,5,6-triaminopyrimidine or 4-hydroxy-2,5,6-triaminopyrimidine sulfate.

Preferred coupler compounds are m-phenylendiamine derivatives, naphthole, resorcine and resorcine derivatives, pyrazolone and m-aminophenol derivatives, and most preferably the coupler compounds disclosed in DE 19959479, p. 1, l. 33 to p. 3, l. 11.

The dyes of formula (1a), (1b) and (1c) may also be used together with unsaturated aldehydes as disclosed in DE 19 717 224 (p. 2, l. 50 to l. 66 and on p. 3 l. 8 to l. 12) which may be used as direct dyes or, alternatively together with oxidation dye precursors.

Further preferred for a combination with a dye of formula (1a), (1b) and (1c) are the following oxidation dye precursors:
  the developer/-coupler combination 2,4,5,6-tetraminopyrimidine and 2-methylresorcine for assessing of red shades;
  p-toluenediamine and 4-amino-2-hydroxytoluene for assessing of blue-violet shades;
  p-toluenediamine and 2-amino-4-hydroxyethylaminoanisole for assessing of blue shades;
  p-toluenediamine and 2,4-diamino-phenoxyethynol for assessing of blue shades;
  methyl-4-aminophenol and 4-amino-2-hydroxytoluene for assessing of orange shades;
  p-toluenediamine and resorcine for assessing of brown-green shades;
  p-toluenediamine and 1-naphthol for assessing of blue-violet shades, or
  p-toluenediamine and 2-methylresorcine for assessing of brown-gold shades.

Furthermore, autooxidizable compounds may be used in combination with the dyes of formula (1a), (1b) and (1c).

The dyes of formula (1a), (1b) and (1c) may also be used in combination with naturally occurring dyes.

Furthermore, the dyes of formula (1a), (1b) and (1c) may also be used in combination with capped diazotised compounds.

Suitable diazotised compounds are for example the compounds of formulae (1)-(4) in WO 2004/019897 (bridging gages 1 and 2) and the corresponding watersoluble coupling components (I)-(IV) as disclosed in the same reference on p. 3 to 5.

Furthermore, the dyes of the present invention can also be combined with dyes which are prepared by the reaction of a reactive carbonyl-compound and a CH-acidic compound as described in DE 10 2006 062 435 A1, WO 00038638, DE 10241076 and WO 05120445;
  with thiadiazol dyes as described in DE 10 2006 036898 and DE 10 2005 055496,
  with fluorescent stilbenic sulphur dyes as described in for example WO 07110532, WO 07110542,
  with tetraazapentamethine dyes as described in WO 07071684 and WO 07071686,
  with dimeric cationic dyes as described in FR 2879195, FR 2879127, FR 2879190, FR 2879196, FR 2879197, FR 2879198, FR 2879199, FR 2879200, FR 2879928, FR 2879929, WO 06063869,
  with azo and styryl dyes as described in EP 0850636,
  with polymeric anionic dyes as described in FR 2882929, with disulfide dyes as described in WO 0597051, EP 1647580, WO 06136617,
with thiol dyes as described in WO 07025889, WO 07039527, and
with conductive polymers as described in US 20050050650, U.S. Pat. No. 7,217,295

The present invention also relates to formulations, which are used for the dyeing of organic materials, preferably keratin-containing fibers, and most preferably human hair, comprising at least one dye of formula (1a), (1b) and (1c).

Preferably the dyes of formula (1a), (1b) and (1c) are incorporated into the composition for treating organic material, preferably for dyeing in amounts of 0.001-5% by weight (hereinafter indicated merely by "%"), particularly 0.005-4%, more particularly 0.1-3%, based on the total weight of the composition.

The dyeing compositions of the present invention are applied on the hair in a temperature range of 10 to 200, preferably 18 to 80, and most preferably from 20 to 40° C.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, I. 16 to 31.

The pH value of the ready-to-use dyeing compositions is usually from 2 to 11, preferably from 5 to 10.

Suitable cosmetic hair-care formulations are hair-treatment preparations, e.g. hair-washing preparations in the form of shampoos and conditioners, hair-care preparations, e.g. pre-treatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers.

Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, I. 70 to col 3, I. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts; for example emulsifiers may be present in the dyeing compositions in concentrations from 0.5 to 30% by weight and thickeners in concentrations from 0.1 to 25% by weight of the total dyeing composition.

Further carriers for dyeing compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, I. 1 to p. 244, I. 12.

If the dyes of formula (1a), (1b) and (1c) are used together with oxidation dyes and/or the addition salts thereof with an acid, they may be stored separately or together. Preferably the oxidation dyes and the direct dyes which are not stable to reduction or base are stored separately.

The dyes of formula (1a), (1b) and (1c) may be stored in a liquid to paste-like preparation (aqueous or non-aqueous) or in the form of a dry powder.

When the dyes are stored separately, the reactive components are intimately mixed with one another directly before use. In the case of dry storage, a defined amount of hot (from 50 to 80° C.) water is usually added and a homogeneous mixture prepared before use.

The dyeing compositions according to the invention may comprise any active ingredients, additives or adjuvants known for such preparations, like surfactants, solvents, bases, acids, perfumes, polymeric adjuvants, thickeners and light stabilisers.

The following adjuavents are preferably used in the hair dyeing compositions of the present invention:-non-ionic polymers, cationic polymers, acrylamide/dimethyldiallylammonium chloride copolymers, diethyl-sulfate-quaternised dimethylaminoethyl methacrylate/vinyl-pyrrolidone copolymers, vinylpyrrolidone/imidazolinium methochloride copolymers; quaternised polyvinyl alcohol, zwitterionic and amphoteric polymers, anionic polymers, thickeners, structuring agents, hair-conditioning compounds, protein hydrolysates, perfume oils, dimethyl isosorbitol and cyclodextrins, solubilisers, anti-dandruff active ingredients, substances for adjusting the pH value, panthenol, pantothenic acid, allantoin, pyrrolidone carboxylic acids and salts thereof, plant extracts and vitamins, cholesterol; light stabilisers and UV absorbers, consistency regulators, fats and waxes, fatty alkanolamides, polyethylene glycols and polypropylene glycols having a molecular weight of from 150 to 50 000, complexing agents, swelling and penetration substances, opacifiers, pearlising agents, propellants, antioxidants, sugar-containing polymers, quaternary ammonium salts and bacteria inhibiting agents.

The dyeing compositions according to the present invention generally comprise at least one surfactant. Suitable surfactants are zwitterionic or ampholytic, or more preferably anionic, non-ionic and/or cationic surfactants.

A further embodiment of the present invention relates to the dyeing of keratin-containing fibers.

The processes comprises
(a) treating the keratin-containing fiber with at least one dye of formula (1a), (1b) and (1c) and
(b) leaving the fiber to stand and then rinsing the fiber.

The dyes of formula (1a), (1b) and (1c) are suitable for all-over dyeing of the hair, that is to say when dyeing the hair on a first occasion, and also for re-dyeing subsequently, or dyeing of locks or parts of the hair.

The dyes of formula (1a), (1b) and (1c) are applied on the hair for example by massage with the hand, a comb, a brush, or a bottle which is combined with a comb or a nozzle.

In the processes for dyeing according to the invention, whether or not dyeing is to be carried out in the presence of a further dye will depend upon the color shade to be obtained.

Further preferred is a process for dyeing keratin-containing fibers which comprises treating the keratin-containing fiber with at least one dye of formula (1a), (1b) and (1c), a base and an oxidizing agent.

A preferred embodiment for dyeing keratin-containing fibers, in particular human hair, with a dye of formula (1a), (1b) and (1c) and an oxidizing agent, comprises $a_1$) treating the keratin-containing fiber with the oxidizing agent, which optionally contains at least one dye of formula (1a), (1b) and (1c), $b_1$) treating the keratin-containing fiber with an oxidizing agent free composition, which optionally contains at least one dye of formula (1a), (1b) and (1c); or alternatively $a_2$) treating the keratin-containing fiber with an oxidizing agent free composition, which optionally contains at least one dye of formula (1a), (1b) and (1c);

$b_2$) treating the keratin-containing fiber with an oxidizing agent, which optionally contains least one dye of formula (1a), (1b) and (1c), with the proviso that at least in one of the process steps $a_1$), $a_2$), $b_1$) or $b_2$) a dye of formula (1a), (1b) and (1c) is present.

In general, the oxidizing agent containing composition is left on the fiber for 0 to 45 minutes, in particular for 15 to 30 minutes at 15 to 45° C.

The oxidizing agent free composition usually comprises customary adjuvants and additives. Preferred are those, which are described in German Patent Application, in col 3, I. 17 to I. 41.

In general, the dye of formula (1a), (1b) and (1c) and the oxidizing agent free composition are left on the fiber for 5 to 45 minutes, in particular for 10 to 25 minutes at 15 to 50° C.

One preferred embodiment of the process is to wash the hair after dyeing with a shampoo and/or a weak acid, such as citric acid or tartrate acid.

The dyes of formula (1a), (1b) and (1c) which are stable to reduction can be stored together with the oxidizing agent free compositions and may be applied as a single composition.

Advantageously the compositions comprising a dye of formula (1a), (1b) and (1c) which are not stable to reduction are prepared with the oxidizing agent free composition just before the dyeing process.

In a further embodiment, the dye of formula (1a), (1b) and (1c) and the oxidizing agent free composition may be applied simultaneously or in succession.

Customary, the oxidizing agent containing composition is evenly applied in a sufficient amount related to the amount of hair, usually in amounts of 30 to 200 g.

Oxidizing agents are for example persulfate or dilute hydrogen peroxide solutions, hydrogen peroxide emulsions or hydrogen peroxide gels, alkaline earth metal peroxides, organic peroxides, such as urea peroxides, melamine peroxides, or alkalimetalbromat fixations are also applicable if a shading powder on the basis of semi-permanent, direct hair dyes is used.

Further preferred oxidizing agents are oxidizing agents to achieve lightened coloration, as described in WO 97/20545, especially p. 9, I. 5 to 9, oxidizing agents in the form of permanent-wave fixing solution, as described in DE-A-19 713 698, especially p. 4, I. 52 to 55, and I. 60 and 61 or EP-A-1062940, especially p. 6, I. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% by weight the corresponding composition.

The oxidizing agents may be present in the dyeing compositions according to the invention preferably in an amount from 0.01% to 6%, especially from 0.01% to 3%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

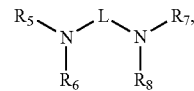

wherein

L is a propylene residue, which may be substituted with OH or $C_1$-$C_4$alkyl; and $R_5$, $R_6$, $R_7$ and $R_8$ independently or dependently from each other are hydrogen; $C_1$-$C_4$alkyl; or hydroxy-($C_1$-$C_4$)alkyl.

The pH-value of the oxidizing agent containing composition is usually about 2 to 7, and in particular about 2 to 5.

One preferred method of applying formulations-comprising the dyes of formula (1a), (1b) and (1c) on the keratin-containing fiber, preferably the hair is by using a multi-compartment dyeing device or "kit" or any other multi-compartment packaging system, as described for example in WO 97/20545 on p. 4, I. 19 to I. 27.

Generally the hair is rinsed after treatment with the dyeing solution and/or permanent-wave solution.

A further preferred embodiment of the present invention relates to a method of dyeing hair with oxidative dyes, which comprises a. mixing at least one dye of formula (1a), (1b) and (1c) and optionally at least one coupler compound and at least one developer compound, and an oxidizing agent, which optionally contains at least one further dye, and b. contacting the keratin-containing fibers with the mixture as prepared in step a.

For adjusting the pH-value organic or inorganic acids, as for example described in DE 199 59 479, col 3, I. 46 to I. 53 are suitable.

Furthermore, the present invention relates to a process of dyeing of keratin-containing fibers of the dyes of formula (1a), (1b) and (1c) with autooxidable compounds and optionally further dyes.

The process comprises a. mixing at least one autooxidable compound and at least one developer compound and at least one dye of formula (1a), (1b) and (1c) and optionally further dyes, and b. treating the keratin-containing fiber with the mixture prepared in step a.

Furthermore, the present invention relates to a process for dyeing keratin-containing fibers with the dyes of formula (1a), (1b) and (1c) and capped diazotised compounds, which comprises, a. treating the keratin-containing fibers under alkaline conditions with at least one capped diazotised compound and a coupler compound, and optionally a developer compound ad optionally an oxidizing agent, and optionally in the presence of a further dye, and optionally with at least one dye of formula (1a), (1b) and (1c), and b. adjusting the pH in the range of 6 to 2 by treatment with an acid, optionally in the presence of a further dye, and optionally at least one dye of formula (1a), (1b) and (1c), with the proviso that at least in one step a. or b. at least one dye of formula (1a), (1b) and (1c) is present.

The capped diazotised compound and coupler compound and optionally the oxidizing agent and developer compound can be applied in any desired order successively or simultaneously.

Preferably, the capped diazotised compound and the coupler compound are applied simultaneously, in a single composition.

"Alkaline conditions" denotes a pH in the range from 8 to 10, preferably 9-10, especially 9.5-10, which are achieved by the addition of bases, for example sodium carbonate, ammonia or sodium hydroxide.

The bases may be added to the hair, to the dye precursors, the capped diazotised compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

The alkaline dyeing compositions of step a. and the acid dyeing compositions of step b. are left on the fiber for 5 to 60 minutes at 15 to 45° C., in particular for 5 to 45 minutes at 20 to 30° C.

Furthermore, the present invention relates to a process for dyeing keratin-containing fibers with the dyes of formula (1a), (1b) and (1c) and at least one acid dye.

The following examples serve to illustrate the processes for dyeing without limiting the processes thereto. Unless specified otherwise, parts and percentages relate to weight. The amounts of dye specified are relative to the material being dyed.

PREPARATION EXAMPLES

Example A1

Step 1

Condensation

To a suspension of 76 g 4-hydrazino-benzoic acid in 1 L of isopropanol 54 g of 4-pyridin aldehyde are added slowly.

The reaction mixture is stirred for ½ h at room temperature and 2 h at 60° C.

After cooling to room temperature the product is isolated by filtration, washed with isopropanol and water and finally dried under vacuum at 60° C., to obtain 119 g of a yellow powder which corresponds to formula

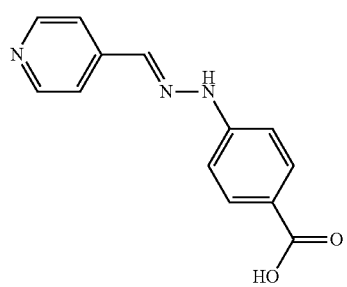

(101a)

LC-MS: m/z=242, $\lambda_{max}$=413 nm, $^{13}$C nmr (dmso-d$_6$): δ [ppm] 167.130, 148.946, 147.971, 143.478, 135.532, 131.143, 121.599, 120.202, 111.862.

Step 2

Alkylation

The product obtained in step 1 is suspended in 70 ml water, the pH is adjusted to >12 and the reaction mixture is cooled to 15-18° C.

Then 153 g of dimethyl sulfate are added slowly, while the pH is maintained at 12-12.5. The reaction mass is stirred for 18 h at room temperature. During this time the pH is maintained at 12-12.5.

Then the reaction mass is stirred at 45° C.

After 2 h the product is precipitated by addition of hydrochloric acid, filtered off and washed with a diluted sodium chloride solution.

After drying 82 g of an orange powder of formula (102b) are obtained.

LC-MS: m/z=270, λ max=413 nm, $^{13}$C nmr (dmso-d$_6$): δ [ppm] 166.865, 150.600, 149.246, 145.045, 130.683, 128.845, 124.499, 122.347, 115.665, 46.810, 34.102.

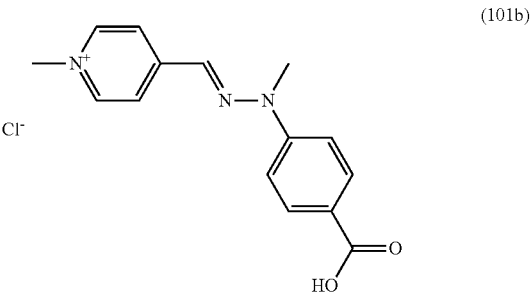

(101b)

Step 3

Chlorination

At room temperature 30.7 g of the product from step 2 are carefully added to 275 ml thionyl chloride.

The reaction mass is stirred for 1 h at room temperature and 1 h at 50° C.

Then the thionyl chloride is removed under reduced pressure to obtain 36 g of a yellow residue of formula (101c).

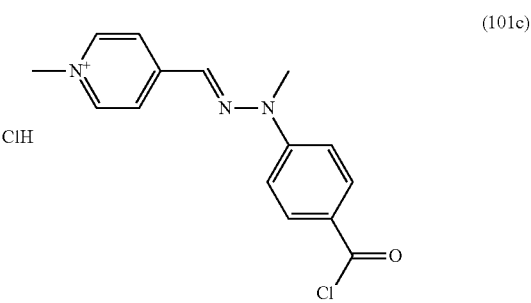

(101c)

The examples A2-A15 have been prepared by reacting the product of step 3 of example A1 with the polymers in Table 1.

TABLE 1

| | |
|---|---|
| Polymer 1 | Polyethyleneimine (PEI) (Aldrich, average $M_n$ 600) |
| Polymer 2 | Polyamin B (Akzo Nobel) |
| Polymer 3 | Lupasol FG (BASF) |
| Polymer 4 | Lupasol PR 8515 (BASF) |
| Polymer 5 | Lupasol G 20 waterfree (BASF) |
| Polymer 6 | Lupasol G 100 |
| Polymer 7 | DADMAC/DAA copolymer (30 wt % DAA, Mn 16.8 kDa) |

Example A2

A solution of 0.29 g of Polymer 1 in 30 ml of water was cooled to 0-5° C. and the pH was adjusted to 11.2. Then 1 g of compound (101 c) was added stepwise, while the pH value was maintained at 11 by addition of 0.5 M NaOH.

When the addition was finished, the reaction mixture was allowed to warm to room temperature.

Then the reaction mixture was neutralized with hydrochloric acid, the solvent was evaporated under vacuum and the residue was dissolved in methanol.

After filtration the solvent was evaporated and the residue was dissolved in water at pH5.

This solution was purified by dialysis (MWCO 1000) to remove low molecular weight impurities. Finally the solvent was evaporated to obtain 0.2 g of a yellow powder.

Example A3

A dispersion of 0.6 g of compound (101c) in 15 ml MEK was added over 4 h in small steps at room temperature to a solution of 0.8 g of polymer 1 in 50 ml isopropanol.

The reaction mixture was stirred for 1 h.

Then 2.7 ml of conc. HCl were added.

The resulting suspension was filtrated and the filter cake was dried to obtain 1.6 g of a yellow powder.

Examples A4-A15 have been prepared following the same procedure as for ex. A3, using the conditions given in Table 2.

TABLE 2

| Ex. | Polymer No. | Amount of Polymer | Amount of Dye (101c) | Solvent | T [° C.] | Time | Yield |
|---|---|---|---|---|---|---|---|
| A4 | 2 | 0.8 g | 0.6 g | 15 ml MEK/50 ml Isopropanol | 23° C. | 4.5 h | 0.9 g |
| A5 | 2 | 0.5 g | 1.9 g | 15 ml MEK/50 ml Isopropanol | 22° C. | 5 h | 1.6 g |
| A6 | 2 | 0.5 g | 1.9 g | 15 ml MEK/50 ml Isopropanol | 22° C. | 4.5 h | 2.08 g |
| A7 | 2 | 0.5 g | 1.9 g | 15 ml MEK/50 ml Isopropanol | 50° C. | 4 h | 1.7 g |
| A8 | 2 | 0.5 g | 1.9 g | 15 ml MEK/50 ml Isopropanol | 0° C. | 4 h | 1.9 g |
| A9 | 2 | 0.5 g | 1.9 g | 15 ml MEK/50 ml Isopropanol | 22° C. | 4.5 h | 1.8 g |
| A10 | 2 | 0.5 g | 0.95 | 12 ml MEK/50 ml Isopropanol | Rt | 4.8 h | 1.4 g |
| A11 | 2 | 0.5 g | 2.6 g | 15 ml MEK/50 ml Isopropanol | Rt | 5 h | 2.5 g |
| A12 | 3 | 0.79 g | 3 g | 18 ml MEK/75 ml Isopropanol | Rt | 4.5 h | 3.4 g |
| A13 | 4 | 0.79 g | 3 g | 20 ml MEK/75 ml Isopropanol | Rt | 4.5 h | 3.4 g |
| A14 | 5 | 0.79 g | 3 g | 18 ml MEK/75 ml Isopropanol | Rt | 4.5 h | 3.5 g |
| A15 | 7 | 1.6 g | 3 g | 18 ml MEK/75 ml Isopropanol | Rt | 4.5 h | 3.2 g |

Example A 16

A solution of 2.34 g of polymer 7 in 40 ml of water was adjusted to pH 11.8 with sodium hydroxide. At 0-5° C. 1 g of the dye (101c) was added slowly as a solid, while the pH was maintained constant. After the addition was completed the temperature was raised to room temperature and stirred over night. The obtained polymer solution was purified by dialysis.

Finally the water was evaporated from the polymer containing fraction under reduced pressure, to obtain 1.62 g of a yellow powder.

Analytics:

The examples A2-A15 have the following $^1$H nmr Signals (MeOH-$d_4$): δ [ppm] 8.7 (br), 8.1 (br), 7.7 (br), 7.5 (br), 4.3 (br), 3.8 (vbr), 3.6 (br).

B. Application Examples

Hair Samples

For the application examples the following hair types have been used:
1 blonde hair tress (VIRGIN White Hair from IMHAIR Ltd., via G. Verga 8, 90134 Palermo (Italy)),
1 middle blonde hair tress (UNA-Europ. nature hair, Color middle blonde from Fischbach & Miller, Postfach 1163, 88461 Laupheim, Germany),
1 bleached hair tress (UNA-Europ. nature hair, Color white bleached blonde from Fischbach & Miller, Postfach 1163, 88461 Laupheim, Germany).
1 gray 85-90% hair tress (International Hair Importers & Products Inc., 251-71 Jericho Turnpike, Bellerose, N.Y. 11426, USA) 1

Coloring Solution:

0.1% w/w of one of the dyes described in examples A2 to A11 (0.2% w/w of dyes A12 to A15) are dissolved in a Plantaren solution (10% w/w Plantacare 200UP (ID: 185971.5) in water; pH adjusted to 9.5 with 50% citric acid solution or monoethanolamine solution).

Dyeing Procedure:

The hair tresses are dyed according to the following procedure:

The coloring solution is applied directly to the dry hair, incubated for 20 min. at room temperature, and then rinsed off under tap water (water temperature: 37° C.+/−1° C.; flow rate of water: 5-6 l/min.).

Then the tresses are pressed out with a paper towel and dried over night at room temperature on a glass plate.

Wash Fastness

For determination of the wash fastness two sets of hair tresses are dyed under the same conditions.

One set of the dyed tresses is washed with a commercial shampoo (GOLDWELL definition Color & Highlights, color-conditioner shampoo) using approx. 0.5 g shampoo for each tress under tap water (water temperature: 37° C.+/−1° C.; flow rate 5-6 l/min).

Finally the tresses are rinsed under tap water, pressed out with a paper towel, combed and dried with a hair dryer or at room temperature.

This procedure is repeated 10 times.

The color position of the colored hair tresses in the CIELAB color coordinate system can be determined spectrophotometrically giving the rectangular coordinates L* (Lightness), a* and b* or alternatively the polar coordinates L*, C* (chroma) and h (hue) [W. Herbst & K. Hunger in Industrial Organic Pigments, VCH Verlagsgesellschaft, 2nd Ed. 1997, page 50 and references therein.

Another reference would be M.-Bohnert et al., Rechtsmedizin (1998) 8, 207-211].

The colorimetric reflectance measurements are conducted with the following spectrophotometer: "Datacolor Spectraflash SF 450" equipped with a xenon light source filtered to D65 with a measurement geometry of diffuse illumination and 8° viewing.

The measurements of the hair tresses are conducted directly on the measure head using the plate with an aperture (hole) of 6.6 mm.

The measurements are conducted 8 times and the average values used.

Before the measurements, the spectrophotometer was calibrated using a black and a white standard provided by Datacolor.

Then the color loss of the set of washed tresses relative to the set of unwashed tresses is evaluated using the Grey Scale according to: Industrial Organic Pigments by Herbst&Hunger, 2nd ed., p. 61, Nr 10: DIN 54 001-8-1982, "Herstellung and Bewertung der Änderung der Farbe", ISO 105-A02-1993.

TABLE 3

Results for Application Examples B1-B14

| Ex. | Dye | Hair Type | Color | Intensity | Brilliance | Washfastness Grey scale | ΔE |
|---|---|---|---|---|---|---|---|
| B1 | A2 | blond | yellow | good | good | 4 | 9.4 |
| | | middle blond | yellow | good | good | 4 | 5.4 |
| | | bleached | yellow | good | good | 4 | 7 |
| B2 | A3 | blond | yellow | good | good | 4 | 7.8 |
| | | middle blond | yellow | good | good | 4-5 | 2.5 |
| | | bleached | yellow | good | good | 4 | 10.1 |
| B3 | A4 | blond | yellow | good | good | 4 | 8 |
| | | middle blond | yellow | good | good | 4-5 | 3.8 |
| | | bleached | yellow | good | good | 4 | 7.2 |
| B4 | A5 | blond | yellow | good | good | 4-5 | 3.8 |
| | | middle blond | yellow | good | good | 4-5 | 4.4 |
| | | bleached | yellow | good | good | 4 | 13 |
| B5 | A6 | blond | yellow | good | good | 4-5 | 4.3 |
| | | middle blond | yellow | good | good | 4-5 | 2.4 |
| | | bleached | yellow | good | good | 4 | 7.1 |
| B6 | A7 | blond | yellow | good | good | 4 | 9.4 |
| | | middle blond | yellow | good | good | 4-5 | 3.1 |
| | | bleached | yellow | good | good | 4 | 7 |
| B7 | A8 | blond | yellow | good | good | 4-5 | 3.1 |
| | | middle blond | yellow | good | good | 4-5 | 2.8 |
| | | bleached | yellow | good | good | 4 | 6.1 |
| B8 | A9 | blond | yellow | good | good | 4-5 | 2.2 |
| | | middle blond | yellow | good | good | 4-5 | 2.9 |
| | | bleached | yellow | good | good | 4 | 5.6 |
| B9 | A10 | blond | yellow | good | good | 3-4 | — |
| | | middle blond | yellow | good | good | 4-5 | — |
| | | bleached | yellow | good | good | 3-4 | — |
| B10 | A11 | blond | yellow | good | good | 4 | 5.1 |
| | | middle blond | yellow | good | good | 4-5 | 2.4 |
| | | bleached | yellow | good | good | 4 | 6.4 |

TABLE 3-continued

Results for Application Examples B1-B14

| Ex. | Dye | Hair Type | Color | Intensity | Brilliance | Washfastness Grey scale | ΔE |
|---|---|---|---|---|---|---|---|
| B11 | A12 | blond | yellow | good | good | 4-5 | 6.5 |
| | | middle blond | yellow | good | good | 4-5 | 7.9 |
| | | bleached | yellow | good | good | 3-4 | 12 |
| B12 | A13 | blond | yellow | good | good | 5 | 3.8 |
| | | middle blond | yellow | good | good | 5 | 3.9 |
| | | bleached | yellow | good | good | 4 | 9.2 |
| | | gray 90% | yellow | good | good | 4 | 6.8 |
| B13 | A14 | blond | yellow | good | good | 5 | 3.1 |
| | | middle blond | yellow | good | good | 5 | 3.3 |
| | | bleached | yellow | good | good | 4 | 8.9 |
| | | gray 90% | yellow | good | good | 4 | 9.1 |
| B14 | A15 | blond | yellow | good | good | 3-4 | 13 |
| | | middle blond | yellow | good | good | 4-5 | 3.2 |
| | | bleached | yellow | good | good | 4 | 15 |
| | | gray 90% | yellow | good | good | 4 | 7.5 |
| B15 | A16 | blond | yellow | good | Moderate | 3 | 8.8 |
| | | middle blond | yellow | good | Moderate | 4 | 3.8 |
| | | bleached | yellow | good | moderate | 3 | 11.6 |

Mixtures of Polymeric Dyes (Ex. B16-B28)

Example B16

A solution of 0.1% w/w of yellow A 9, a solution of 2% w/w red A7 in GB2440219 and a solution of blue A9 in PCT/EP2009/066421 are mixed in a ratio 3.5, 0.7 and 2.5. The brown solution is applied to human hair.

| Ex. | Dye | Hair Type | Color | Intensity | Brilliance | Washfastness Grey scale | ΔE |
|---|---|---|---|---|---|---|---|
| B29 | A9 with red and blue | blond | brown | good | good | 4 | 7.2 |
| | | middle blond | brown | good | good | 4 | 6.8 |
| | | bleached | brown | good | good | 4-5 | 2.7 |

Example B17

A solution of 0.2% w/w of yellow A 9, and a solution of 0.2% w/w red A7 in GB2440219 are mixed in a ratio 1:1. The orange solution is applied to human hair.

| Ex. | Dye | Hair Type | Color | Intensity | Brilliance | Washfastness Grey scale | ΔE |
|---|---|---|---|---|---|---|---|
| B30 | A9 with red | blond | red | good | good | 4 | 8.1 |
| | | middle blond | red | good | good | 4-5 | 4.8 |
| | | bleached | red | good | good | 4 | 6.6 |

A dye emulsion, pH=10.5

| INGREDIENT | w/w % |
|---|---|
| Mixture of dyes as described in table 4 and 5 | x |
| Cetearyl Alcohol | 12.00 |
|Ceteareth-20 | 4.50 |

-continued

| INGREDIENT | w/w % |
|---|---|
| Polysorbate 60 | 2.30 |
| Glyceryl Stearate SE | 2.00 |
| Sorbitan Stearate | 0.75 |
| Oleth-5 | 1.25 |
| Caprylic/Capric Triglyceride | 0.50 |
| Disodium EDTA | 0.05 |
| Monoethanolamine 99% | 0.90 |
| Ammonium Hydroxide 29% | 6.60 |
| Dihydroxypropyl PEG-5 Linoleammonium Chloride | 0.50 |
| Hydrolyzed Soy Protein 20% | 0.50 |
| Fragrance Drom 847 735 - Day at the Beach | 0.50 |
| Deionized Water 70° C. | ad 100.00 | is mixed with 1.5 wt. % of a 9% hydrogen peroxide solution and the mixture is immediately applied to a tress of brown hair.

After 30 minutes the tress is rinsed, shampooed, rinsed and dried.

The color of the dyed tresses is given in Tables 4 and 5.

TABLE 4

Mixtures of polymeric dyes.

| Comp. of formula | Color | Formulation No.: | | | | |
|---|---|---|---|---|---|---|
| | | B18 | B19 | B20 | B21 | B22 |
| A14 | yellow | 0.1 | 5.0 | | | 0.03 |
| A23-EP2007/056945 [2] | orange | 1.0 | | 0.4 | 0.07 | |
| A7-EP2007/056945 [2] | red | | 0.5 | | | 0.03 |
| A9-EP2007/056945 [2] | red | | | 0.3 | | |
| A15-EP2007/056945 [2] | red | | | | 0.01 | |
| A15-WO09/090124 [3] | blue | 1.0 | | | | 0.03 |
| A20-WO09/090124 [3] | blue | | 2.0 | | | |
| A23-WO09/090124 [3] | blue | | | | 0.1 | |
| A40-WO09/090124 [3] | blue | | | | | 0.03 |
| Total dye content X | | 0.3 | 7.5 | 0.8 | 0.11 | 0.09 |
| Color result on bleached hair [1] | | S | B | B | B | B |

[1] S = black, B = brown
[2] Polymeric dyes described in patent application no. EP2007/056945.
[3] Polymeric dyes described in patent application no. WO09/090124

TABLE 5

Mixtures of polymeric dyes and direct dyes.

| Comp. of formula | Formulation No.: | | | | | | | |
|---|---|---|---|---|---|---|---|---|
| | B23 | B24 | B25 | B26 | B27 | B28 | B29 | B30 |
| A13 | | 5.0 | | | 0.4 | 2.0 | 0.5 | |
| Direct Dye | | | | | | | | |
| C.I. Basic Blue 99 | | 2.0 | | 0.2 | 0.01 | 1.6 | 0.1 | 0.2 |
| C.I. Basic Blue 124 | 0.1 | | 0.5 | | 1.0 | | | |
| Basic Red 76 | 0.2 | | | 0.2 | | | 0.3 | |
| HC Red No.3 | | | 0.1 | | | 0.1 | | |
| HC Red BN | | 0.5 | | | | 0.1 | | 0.1 |
| Basic Brown 16 | 0.1 | | | | 0.5 | | | |
| Basic Brown 17 | 0.1 | | | | 0.5 | 2.0 | | 0.5 |
| Total dye content X | 0.5 | 7.5 | 0.6 | 0.4 | 2.41 | 0.5 | 0.3 | 0.8 |
| Color result on bleached hair [1] | B | B | V | V | B | S | G | B |

[1] S = black, B = brown, V = violet, G = green

In the following examples the abbreviation RKN is a designation of grade and indicates the purity of the cellulose; the abbreviation SR (Schopper-Riegler) indicates the freeness.

Example 31

50 parts of chemically bleached beech sulfite are mixed with 50 parts of bleached RKN 15 (freeness 22 DEG SR) and 2 parts of the dye according to Example A4 in water (pH 6, hardness of water 10 DEG of German hardness, temperature 20 DEG and liquor ratio 40:1).

After stirring for 15 minutes, paper sheets are produced on a Frank sheet-former.

The paper has been dyed in a very intense yellow shade. The effluent is completely colourless. A degree of exhaustion of virtually 100 percent is attained. The fastness properties to light and wet processing are excellent.

Example 32

A paper web composed of bleached beech sulfite pulp (22 DEG SR) is produced on a continuously operating laboratory paper-making machine. An aqueous solution of the dye according to Example A7 is metered continuously into the low-density pulp 10 seconds upstream of the head box, with vigorous turbulence (0.5 percent dyeing, liquor ratio 400:1, hardness of water 10 DEG German hardness, pH 6, temperature 20 DEG).

A deep yellow coloration of medium intensity is formed on the paper web. The effluent is completely colourless.

Example 33

10 parts of cotton fabric (bleached, mercerized cotton) are dyed in a laboratory beam dyeing machine in 200 parts of a liquor (hardness of water 10 DEG German hardness, pH 4, dye liquor circulated three times per minute) containing 0.05 part of the dye according to Example A4. The temperature is raised in the course of 60 minutes from 20 DEG to 100 DEG and is then kept constant for 15 minutes.

The dye liquor is completely exhausted. A deep yellow coloration distinguished by good fastness to light and very good fastness to wet processing is formed on the cotton fabric. A textile fabric composed of regenerated (viscose) is dyed by the same procedure. A deep yellow dyeing which has good fastness to light and very good fastness to wet processing is also obtained on this material by means of the dye of Example A4.

Example 34 of a Purely Solvent-Containing Wood Stain 3.0 parts by weight of the hydrazone dye A15
40.0 parts by weight of ethyl alcohol,
40.0 parts by weight of 1 methoxy-2-propanol and
17.0 parts by weight of isopropanol Example 35 of an Aqueous Wood Stain 3.0 parts by weight of the hydrazone dye A7 are dissolved in 100.0 ml of water containing
0.05 percent by weight Invadin LU (a wetting agent).

The wood stains obtained according to the above Examples are applied by means of a brush to a 10.times.5.5 cm piece of ash wood. The coloured piece of wood is dried in air for 12 hours.

The invention claimed is:

1. Polymeric dye of formula

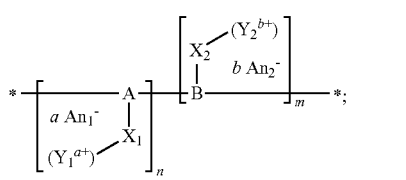
(1a)

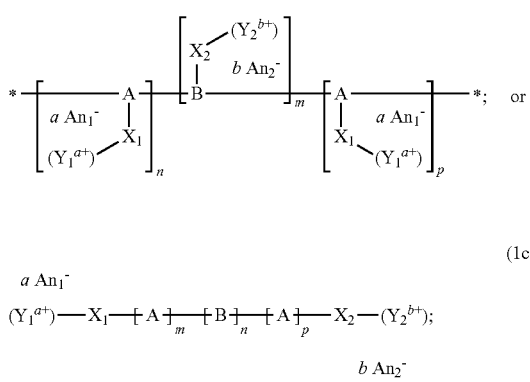
(1b); or (1c)
$a\, An_1^-$
$(Y_1^{a+}) - X_1 - [A]_m - [B]_n - [A]_p - X_2 - (Y_2^{b+});$
$b\, An_2^-$ wherein A and B, independently from each other represent a polymer backbone;

$X_1$ and $X_2$ independently from each other are a linkage group selected from —S—, —S—S—, —N—, —N=—, —N($R_5$)—, —S(O)—, —SO$_2$—, —(CH$_2$CH$_2$—O)$_{1-5}$—, —(CH$_2$CH$_2$CH$_2$—O)$_{1-5}$—, —C(O)—, —C(O)O—, —OCO—,

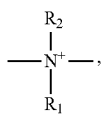

—CON($R_1$)—, —C(N$R_1R_2$)$_2$—, —($R_1$)NC(O)—, —C(S)$R_1$—; which may be interrupted and/or terminated at one or both ends by one or more than one —C$_1$-C$_{30}$alkylene- or —C$_2$-C$_{12}$alkenylene-; or an optionally substituted, saturated or unsaturated, fused or non-fused aromatic or nonaromatic (heterocyclic) bivalent radical optionally comprising at least one heteroatom; a saturated or unsaturated, fused or non-fused aromatic or nonaromatic bivalent radical comprising at least one heteroatom, which is optionally substituted by C$_1$-C$_{30}$alkyl, C$_1$-C$_{30}$alkoxy, C$_2$-C$_{12}$alkenyl, C$_5$-C$_{10}$aryl, C$_5$-C$_{10}$cycloalkyl, C$_1$-C$_{10}$alkyl(C$_5$-C$_{10}$arylene), hydroxy or halogen;

$R_1$ and $R_2$ independently from each other are hydrogen; unsubstituted or substituted, straight-chain or branched, monocyclic or polycyclic, interrupted or uninterrupted C$_1$-C$_{14}$alkyl; C$_2$-C$_{14}$alkenyl; C$_6$-C$_{10}$aryl; C$_6$-C$_{10}$aryl-C$_1$-C$_{10}$alkyl; or C$_5$-C$_{10}$alkyl(C$_5$-C$_{10}$aryl);

$Y_1$ and $Y_2$ independently from each other are a residue of an organic dye selected from hydrazone dyes of formula

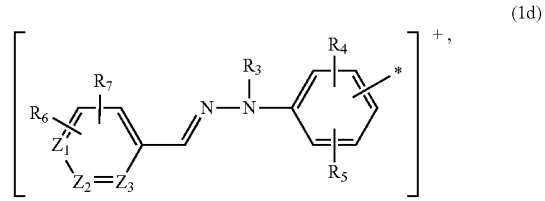
(1d)

wherein $Z_1$, $Z_2$ and $Z_3$, independently from each other are —CR$_8$— or —NR$_9^+$—; and at least one of $Z_1$, $Z_2$ or $Z_3$ is —NR$_9^+$—; wherein at least one of $Y_1$ and $Y_2$ is a residue of an organic dye;

R, $R_3$, $R_4$, $R_5$, $R_6$, $R_7$, $R_8$ and $R_9$ independently from each other are hydrogen; hydroxy; C$_1$-C$_5$alkyl; hydroxy-C$_1$-C$_5$alkyl; C$_1$-C$_5$alkoxy; —NO$_2$; —Cl; —Br; —COOH; —SO$_3$H; —CN; NH$_2$; or CH$_3$—CO—NH—;

$An_1$, $An_2$ and $An_3$, independently from each other are an anion;

a and b independently from each other are a number from 1 to 3;

m is a number from 0 to 5000;

n is a number from 0 to 5000; and p is a number from 1 to 5000;

wherein the sum of m+n+p≧3.

2. Dye according to claim 1, wherein $Y_1$ and $Y_2$ correspond to the formula

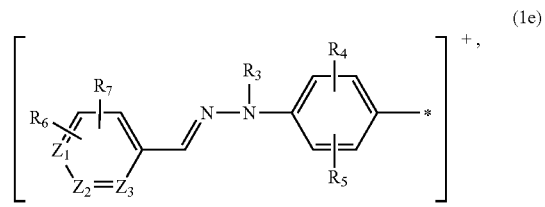
(1e)

wherein $Z_1$, $Z_2$ and $Z_3$, R, $R_3$, $R_4$, $R_5$, $R_6$, $R_7$, $R_8$ and $R_9$ are defined as in claim 1.

3. Dye according to claim 1, wherein $Y_1$ and $Y_2$ correspond to the formula

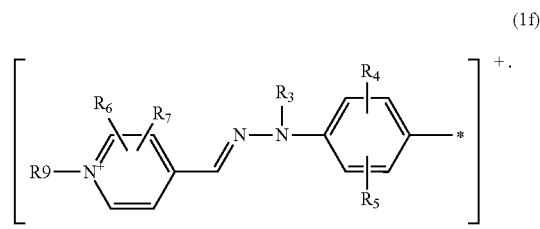
(1f)

4. Dye according to claim 1, wherein $Y_1$ and $Y_2$ have the same meaning.

5. Dye according to claim 1, wherein $X_1$ and $X_2$ independently from each other are a linkage group selected from —SO$_2$— and —C(O)—.

6. Dye according to claim 1, wherein

A and B, independently from each other are selected from polyethylenimine, polypropyleneimine, polyvinylamine; polyvinylimine; polysiloxane; polystyrene, polyvinylimidazol, polyvinylpyridine, copolymers of vinylimidazole or vinylpyridin and vinylpyrrolidone, DADMAC/DAA copolymers, polyetheramines, polyvinylalcohol, polyacrylate, polymethacrylate; polyurethanes derived from hydroxyl-terminated polyethers, polyesters or polybutadienes on the one hand and aliphatic or aromatic polyisocyanates on the other, as well as precursors thereof; polyamides and copolyamides derived from diamines and dicarboxylic acids and/or from aminocarboxylic acids or the corresponding lactams; polysaccharide, starch, cellulose, lignin; and copolymers and blends of the mentioned polymers.

7. Dye according to claim 1, wherein the molecular weight of the polymeric dye is from 400 to 50000.

8. Dye according to claim 1, wherein the dyes correspond to formula

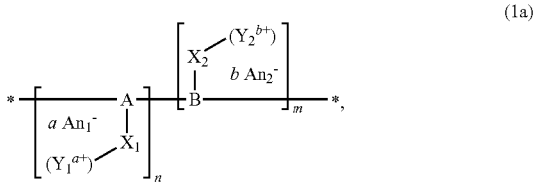

(1a)

wherein

A and B, independently from each other represent a polymer backbone;

$X_1$ and $X_2$ independently from each other are a linkage group selected from —$SO_2$— and —C(O)—;

$Y_1$ and $Y_2$ independently from each other are a radical of formula (1f);

a and b independently from each other are a number from 1 to 3;

m is a number from 0 to 5000;

n is a number from 0 to 5000; and wherein the sum of m+n≧2.

9. A composition comprising at least one dye of formula (1a), (1b) or (1c) as defined in claim 1.

10. A composition according to claim 9 comprising in addition at least one single further direct dye and/or an oxidative agent.

11. A composition according to claim 9 in form of a shampoo, a conditioner, a gel or an emulsion.

12. A method of dyeing organic material, which comprises treating the organic material with at least one dye of formula (1a), (1b) or (1c) according to claim 1.

13. The method according to claim 12, which comprises treating the organic material with at least one dye of formula (1a), (1b) or (1c) as defined in claim 1 and an oxidative agent and, optionally, a further direct dye.

14. The method according to claim 12, which comprises treating the organic material with at least one compound of formula (1a), (1b) or (1c) as defined in claim 1 and at least one single oxidative dye, or treating the organic material with a dye of formula (1a), (1b) or (1c) as defined in claim 1 and at least one single oxidative dye and an oxidative agent.

15. The method according to claim 12 wherein the organic material is human hair.

16. The method according to claim 12, wherein the organic material is wool, leather, textiles, paper or wood.

17. A method of dyeing organic material, which comprises treating the organic material with a composition according to claim 9.

* * * * *